US005668887A

United States Patent [19]
Parker et al.

[11] Patent Number: 5,668,887
[45] Date of Patent: Sep. 16, 1997

[54] COATING DENSITY ANALYZER AND METHOD USING NON-SYNCHRONOUS TDI CAMERA

[75] Inventors: H. Galen Parker, Rochester; Richard Dean Young, Fairport, both of N.Y.

[73] Assignee: Eastman Kodak Company, Rochester, N.Y.

[21] Appl. No.: 425,640

[22] Filed: Apr. 20, 1995

Related U.S. Application Data

[63] Continuation-in-part of Ser. No. 891,318, May 29, 1992, Pat. No. 5,533,139.

[51] Int. Cl.$^6$ .................................................. G01N 21/00
[52] U.S. Cl. ............................................. 382/108; 382/141
[58] Field of Search .................................... 382/108, 141

[56] References Cited

U.S. PATENT DOCUMENTS

| | | | |
|---|---|---|---|
| 4,118,730 | 10/1978 | Lemelson | 358/93 |
| 4,223,346 | 9/1980 | Neiheisel et al. | 358/106 |
| 4,274,748 | 6/1981 | Burtin et al. | 356/431 |
| 4,314,275 | 2/1982 | Chapman | 358/113 |
| 4,319,270 | 3/1982 | Kimura et al. | 358/106 |
| 4,327,377 | 4/1982 | Takken | 358/199 |
| 4,382,267 | 5/1983 | Angle | 358/213 |
| 4,442,457 | 4/1984 | Pines | 358/213 |
| 4,511,918 | 4/1985 | Lemelson | 358/107 |
| 4,575,632 | 3/1986 | Lange | 250/334 |
| 4,595,840 | 6/1986 | Puumalainen | 250/572 |
| 4,679,075 | 7/1987 | Williams et al. | 358/106 |
| 4,714,963 | 12/1987 | Vogel | 358/213.26 |
| 4,724,481 | 2/1988 | Nishioka | 358/106 |
| 4,771,333 | 9/1988 | Michaels | 358/213.29 |
| 4,827,142 | 5/1989 | Hatje | 250/563 |
| 4,879,752 | 11/1989 | Aune et al. | 382/1 |
| 4,896,211 | 1/1990 | Hunt et al. | 358/106 |
| 4,922,337 | 5/1990 | Hunt et al. | 358/101 |
| 4,949,172 | 8/1990 | Hunt et al. | 358/101 |
| 4,950,911 | 8/1990 | Williams et al. | 250/563 |
| 4,952,809 | 8/1990 | McEwen | 250/342 |
| 4,958,223 | 9/1990 | Juvinall et al. | 358/106 |
| 5,023,714 | 6/1991 | Lemelson | 358/107 |
| 5,033,095 | 7/1991 | Marcantonio | 382/8 |
| 5,040,057 | 8/1991 | Gilblom et al. | 358/101 |
| 5,113,260 | 5/1992 | Tandon | 358/213.11 |
| 5,119,190 | 6/1992 | Lemelson | 358/93 |
| 5,132,791 | 7/1992 | Wertz et al. | 358/106 |
| 5,533,139 | 7/1996 | Parker et al. | 382/108 |
| 5,548,120 | 8/1996 | Parker et al. | 250/341.7 |

OTHER PUBLICATIONS

"How TDI Works", DALSA, Inc. manual pp. 78–79, Nov. 19, 1991.

*Primary Examiner*—Melvin Marcelo
*Attorney, Agent, or Firm*—William F. Noval

[57] ABSTRACT

An image processor based system and method for recognizing predefined-types of coating density imperfections in a web, specifically continuous type or streak imperfections. Continuous type imperfections are recognized in a continuous web moved at a certain rate through an imaging region illuminated by a stripe of substantially constant illumination. A time-delay integrating CCD camera is focused on the illuminated imaging region. The TDI CCD camera comprises an array of N rows of M light sensitive CCD elements each imaged on a fixed discrete pixel-related image area of the illuminated imaging region. The charge levels accumulated in the CCD elements of each row are shifted to the succeeding row or CCD elements and summed with the charge levels therein at a line shift clock frequency that ensures that an asynchronous relationship exists with respect to the incremental movement of the web. During the clock cycle of the N rows, the corresponding pixel areas of the illuminated web shift asynchronously or creep through the discrete pixel-related image areas. The accumulated pixel charge values derived from the pixel-related image areas of the illuminated region of said moving web emphasize imaging of longitudinal streak imperfections in the web due to the asynchronous movement the web.

17 Claims, 4 Drawing Sheets

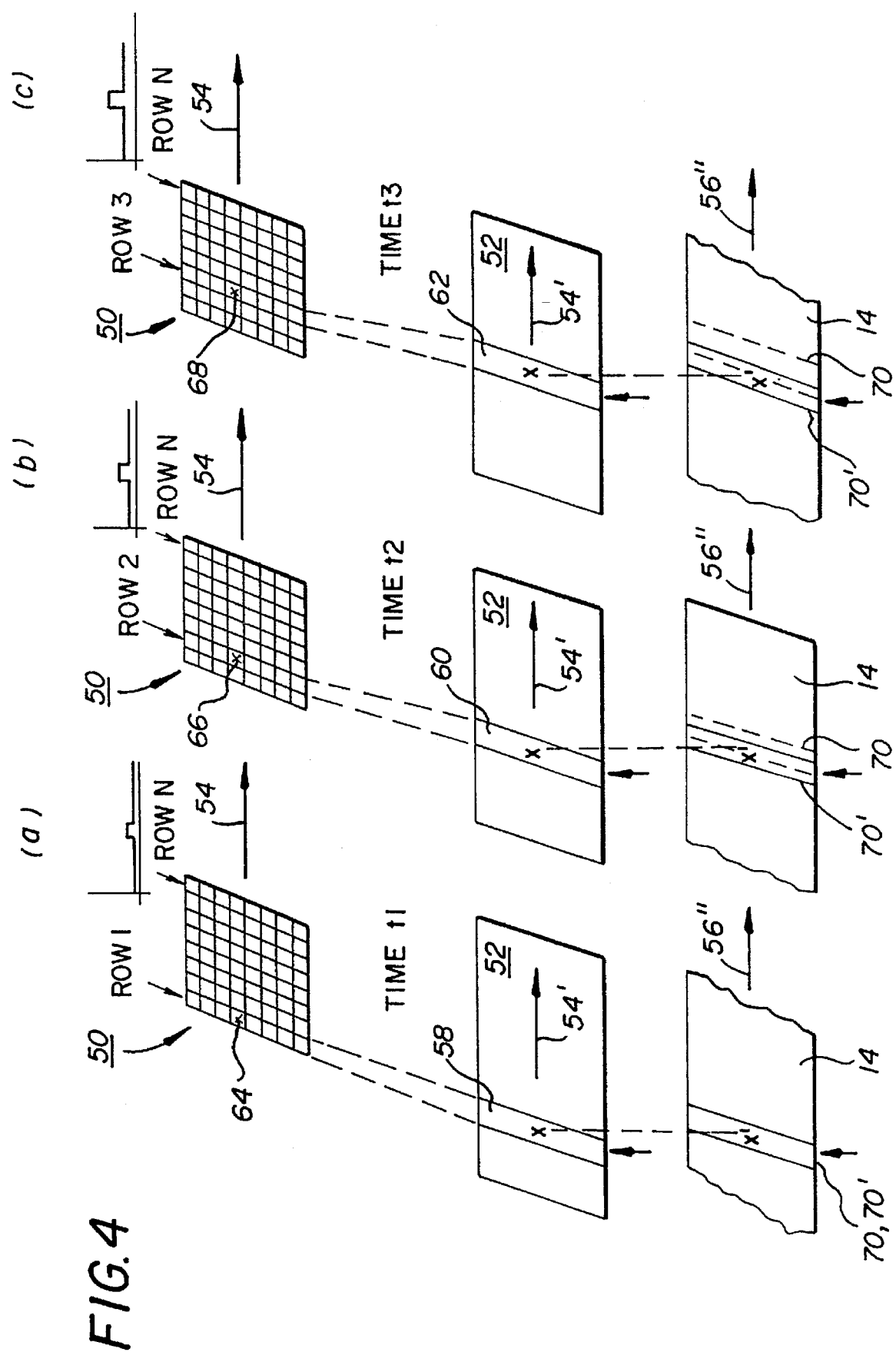

COATING DENSITY ANALYZER AND METHOD USING NON-SYNCHRONOUS TDI CAMERA

REFERENCE TO PARENT APPLICATION

This application is a continuation-in-part application of commonly assigned, U.S. patent application Ser. No. 891,318 filed May 29, 1992 and entitled COATING DENSITY ANALYZER AND METHOD USING IMAGE PROCESSING, now U.S. Pat. No. 5,533,139, issued Jul. 2, 1996.

REFERENCE TO CO-PENDING APPLICATION

Reference is hereby made to commonly assigned co-pending U.S. patent application Ser. No. 339,052 filed Nov. 14, 1994 for LINEAR INTEGRATING CAVITY LIGHT SOURCE FOR INFRA-RED ILLUMINATION OF SENSITIZED MEDIA by H. G. Parker et al, now U.S. Pat. No. 5,548,120, issued Aug. 20, 1996.

FIELD OF THE INVENTION

This invention relates in general to the detection of coating imperfections on a coated web and, more particularly, to a system and method for recognizing predefined-types of coating imperfections in a web through the acquisition of optical density variation information, for example, from a moving, continuous web substantially uniformly, transmissively illuminated.

DESCRIPTION OF THE BACKGROUND ART

Research and development efforts in the photographic materials and paper materials industries often focus on various types of imperfections in a moving coated web. These imperfections may, for example, result from disturbances in the coating process, such as may occur during the sensitization of photographic film. Research and development efforts attempt to isolate, through process modeling, the source of an on-going disturbance-type in a coating process. Coating imperfections of particular interest to the industries are continuous-type imperfections and point-type imperfections. These imperfection types, which can occur in one or more coating levels on a support web, are typically indicative of a disturbance or design related problem in the coating process. An effective on-line imperfection recognition system and method would enable one to discern, characterize and confirm various models of the coating process, thereby determining the disturbance causing such an imperfection. Two significant issues, however, must be addressed by any imperfection recognition system before adequate optical data can be collected from sensitized coatings under examination. First, the system must be able to extract small density changes from the obtainable spatial and temporal noise background. Secondly, the system must provide adequate illumination within the spectral bandwidth of the usable contrast range, while avoiding fogging of any sensitized web.

State-of-the-art efforts to quantize moving web disturbances have most commonly been implemented as laser scanning systems. For example, continuous laser beams are often swept by multifaceted polygon mirror scanners across moving webs of film or paper support, and focused with dedicated optics onto a discrete detector such as a photomultiplier tube. Various detector configurations enable data acquisition in either a reflective or transmissive mode. Unfortunately, such laser scanner packages can be expensive and typically have limited anomaly detection capabilities. Specifically, such laser scanning packages are almost universally unable to process data associated with very narrow lines and streaks which may be imbedded in the signal noise background. Also, current laser scan output processing packages, in general, remain less sophisticated than those accompanying state-of-the-art imaging technologies, such as solid state cameras.

More recently, CCD cameras have been proposed for use in scanning webs to detect various types of imperfections. A further CCD camera has been developed with a "time-delay integration" or "time-delay integrating" (TDI) function for a variety of uses as described, for example in U.S. Pat. Nos. 4,922,397 and 5,040,057 as well as in U.S. Pat. Nos. 4,314,275, 4,382,267 and 4,952,809. In these patents, the CCD element charges of each row of CCD photosites or elements of the array of elements is shifted to the next row of elements (while maintaining column alignment) by a line shift clock signal. The line shift clock frequency is synchronized with the incremental movement of a discrete pixel-related image area of the web or object being imaged.

FIG. 1 illustrates the synchronous line shift operation with respect to incremental movement of a web or object through an illuminated imaging region 52 over three successive shift clock time cycles t1, t2, and t3 in respective positions (a), (b) and (c). The M column by N row, CCD element array pattern 50 is fixed in position. Each discrete CCD element of the array pattern 50 images a fixed pixel-related image area of the fixed imaging region 52. For example, a discrete pixel-related image area X in successive, adjacent scan lines 58, 60, 62 of the region 52 is imaged by three CCD elements 64, 66, 68 of Row 1, Row 2 and Row 3 in the same column of the array pattern 50 during each shift clock time cycle. Thus, the scan lines 58, 60, and 62 shift in the direction of arrow 54' with the shift effected by the shift clock in the direction of arrow 54.

Each shift clock time cycle t1, t2, and t3, et seq., includes a charge integration time and a charge shift time. During the charge shift time, the time integrated charges of the CCD column elements in each row are transferred or shifted to the corresponding column CCD elements in the next row in the direction of charge accumulation denoted by arrow 54, so that the charge accumulates as shown in the wave shape of accumulated charge during the illustrated three clock time cycles. When the line shift clock completes tN clock time cycles, the total accumulated N charges in Row N are transferred to a shift register (not shown) and then employed to recreate the image line on a monitor or otherwise processed.

In the prior art example of FIG. 1, it is assumed that the object or a segment of the web 14 is moving incrementally at a predetermined fixed rate in the direction of web movement denoted by arrow 56 within the plane of the imaging region 52. The line shift clock frequency is synchronized to the incremental movement of each pixel-related web stripe area 70 into the adjacent (in the column direction) pixel-related scan line 58, 60 and 62. As a result, the same discrete, pixel-related, web area is successively imaged in the pixel-related image areas of the imaging region 52. The pixel-related area X is shown in the positions at time cycles t1, t2, and t3 reflected onto the same position in web stripe area 70. In this way, charges that are dependent on the light intensity reflected from or transmitted by the same pixel-related web area X' accumulate as it is imaged by a CCD column element in each of the N rows of CCD elements.

Although only a single scan line is highlighted in this example, it will be understood that the shift clock signal is applied to all rows simultaneously and that the accumulated charges over the total N rows is shifted into the shift register from row N during each shift clock time cycle. The result of the synchronization of the line shift clock frequency to the incremental motion is to provide a multiple exposure of the web or object to capture a "stop motion" image and avoid any smearing of the image features. This is referred to short hand as a synchronized TDI CCD camera or TDI camera.

As described in the '267 patent, the synchronized TDI CCD camera (or "TDI imager" as used therein) has application in imaging objects, scenes or moving webs (hereafter web, for convenience) in low light level conditions and, in the context of the field of the present invention, in conditions where the web is moving at such a high rate that not enough photoelectric charge can accumulate in each particular CCD element in any given line or row of CCD elements. As described above, the TDI imager sums the charges accumulated by the M parallel CCD elements in a selected set of N rows of M parallel CCD elements at a TDI row or line shift clock signal frequency synchronized to the web advancement. In other words, as the web advances, a scan line of M pixel-related image areas on the web is successively imaged on the M parallel CCD elements of the N rows, and the accumulated charges for each set of N rows are transferred and summed with new charge each time that the web advances to the next row. As a result, the M×N CCD element array may be viewed as a kinear array scanner of M CCD elements imaging a single line of the moving web that is captured N times as the web is advanced.

The TDI function provides an effective gain in sensitivity proportional to the number N of rows of CCD elements contributing to the total summed charges, and random noise attributable to an individual CCD element in any given row is averaged out. In this fashion, enough total charge may be accumulated by the multiple-exposures of the scanned line of the web that a usable contrast image may be created from a display or analysis of the scanned lines of the web. Random noise is reduced approximately in proportion to $\sqrt{N}$ thereby improving the signal/noise ratio of the accumulated charge signal. A two-dimensional display of sections of webs (i.e., discrete scenes or objects in those contexts) may be created on a suitable display or printed out from a composite number of such line scans forming an image frame.

In order to derive a coherent or focused, two dimensional image display or print from the discrete, accumulated charge line scans, the above referenced patents all emphasize the need to synchronize (or derive) the CCD row shift clock signal for transferring the charges of each CCD element in each row of M CCD elements to corresponding CCD element in the next row to the incremental movement of the scanned line of the web. In the '057 patent, the TDI imager disclosed therein may also be selectively switched from this "synchronized mode" to operate in a conventional video camera raster scan mode, or the shift clock signal may be switched to an internal clock, in order to operate the TDI imager in a stationary scan mode or in a mode where an image is "grabbed". This process is described in regard to use of a non-TDI CCD camera and strobe lamp or web position sensor in an earlier U.S. Pat. No. 4,896,211. In either the internal clock or raster scan mode, the TDI imager may be used to derive images of stationary objects, scenes or documents or to initialize or align the TDI imager with respect to a stationary web.

The operation of the synchronous TDI imager provides clear frame images of moving webs, particularly to image specks or holes or other discrete, non-continuous blemishes or imperfections at low light levels which would be insufficient for a non-TDI CCD camera. This capability eliminates the need for strobe lighting and provides full frame images without substantial web image overlap from frame to frame. These characteristics were viewed as desirable in the above-listed patent descriptions. In fact, it is represented that the TDI CCD camera is not optimally usable absent this capability.

A need continues to exist today in the photographic and paper materials industry for a more effective and less expensive technique to extract and characterize imperfections from background data including inherent noise variations, and particularly low-level, narrow continuous-type imperfections in a moving coated web.

SUMMARY OF THE INVENTION

Briefly described, the present invention comprises a coating density analyzer and method using a TDI CCD camera for scanning moving, coated webs without synchronizing the TDI charge transfer clock signal to the movement of the web. The TDI CCD camera is not synchronized to the moving web in order to achieve an image "smear" in the direction of movement that emphasizes and magnifies longitudinal, continuous streak imperfections in coatings or base thicknesses of coated webs.

The invention is realized in apparatus for, and a method of, detecting streak imperfections in moving webs comprising the steps of and means for: moving the web to be imaged in a longitudinal direction of movement through an imaging region at a predetermined rate; illuminating the moving web in the imaging region with light from a light source; providing a time-delay integrating camera having an array of light sensitive, charge-coupled, image sensor elements, each image sensor element providing discrete light sensitive element pixel charge values dependent on the intensity of light impinging thereon from a discrete pixel image area imaged thereon; imaging the imaging region of the illuminated moving web onto said time-delay integrating camera array; shifting the pixel charge values from one discrete light sensitive element to the next discrete light sensitive element across the array during a shift clock cycle time at a shift clock frequency asynchronously related to the rate of movement of the web through the imaging region such that the discrete pixel areas of imaging region imaged by successive light sensitive elements across the array change over the time that the pixel charge values are shifted and summed through all of the successive light sensitive elements; shifting the pixel charge values from one discrete light sensitive element to the next discrete light sensitive element across the array at a fixed shift frequency asynchronously related to the rate of movement of the web through the imaging region and summing the shifted charge values, such that the discrete pixel image areas of the web imaged by successive light sensitive elements across the array change over the time that the pixel charge values are shifted and summed through all of the successive light sensitive elements in the same row; accumulating the shifted and summed pixel charge values from all of the rows of light sensitive elements as accumulated pixel charge values; and processing the accumulated pixel charge values to provide an enhanced image of imperfections in the moving web extending in the direction of movement.

Stated another way, the invention is realized in apparatus for, and a method of, detecting streak imperfections in moving webs employing a time-delay integrating camera comprising the means for and steps of: moving a web to be imaged through an imaging region at a predetermined rate in a longitudinal direction of movement; illuminating the moving web in the imaging region with light from a light source; providing a line shift clock signal defining a clock time cycle during which the moving web is moved in the longitudinal direction an incremental distance; focusing an imaging region of the moving illuminated web onto a time-delay integrating camera having an array of light sensitive, charge-coupled, image sensor elements, comprising a plurality of N rows of M image sensor elements, each image sensor element integrating light from a discrete fixed pixel-related image area of the imaging region, as the web is moving the incremental distance through the pixel-related image area, into a corresponding pixel charge value over a clock time cycle; and operating the time-delay integrating camera asynchronously in with respect to the predetermined rate of movement of the web, such that the accumulated pixel charge values derived from the focused pixel images of the illuminated region of the moving web emphasizes imaging of longitudinal streak imperfections in the web due to the movement in the longitudinal direction of the web through the N successive incremental distances.

Preferably the means for and step of providing the display further comprises: serializing the accumulated pixel values in the shift register to produce video image horizontal scan lines; producing a video display of the projected image of the illuminated region of the moving web from the video image horizontal scan lines; and monitoring the video display to detect streak imperfections in the moving web emphasized by the movement of the web at the predetermined rate during each clock cycle time causing the accumulated pixel values to reflect a longitudinal displacement of the moving web.

ADVANTAGES OF THE INVENTION

The use of a TDI camera operating asynchronously to web speed for imaging moving webs to identify streak imperfections has advantageous effects not recognized in the prior art. An enhanced time exposure of the streak imperfections is achieved accompanied by a significant reduction in background noise. Individual random noise generated at particular CCD elements among the array of M×N CCD elements is averaged out as the charges in the M parallel row pixel elements are summed together over N rows before the sum is transferred to the shift register. The summed pixel charges therefore have a high signal-to-noise ratio. The summed pixel charges also reflect the movement of the pixel-related web areas and so provide a degree of smearing of the image that allows enhanced discrimination of continuous type web imperfections. The asynchronously operated TDI camera eliminates the need for subsequent signal integration.

BRIEF DESCRIPTION OF THE DRAWINGS

These and other objects, advantages and features of the present invention will be more readily understood from the following detailed description of certain preferred embodiments thereof, when considered in conjunction with the accompanying drawings in which:

FIG. 4 is a schematic illustration of the creep of the pixel-related image area of the web being moved in the direction of integrated row transfer with respect to the line shift clock of the rows of elements of the CCD array.

DETAILED DESCRIPTION OF THE PREFERRED EMBODIMENTS

Figure 1:
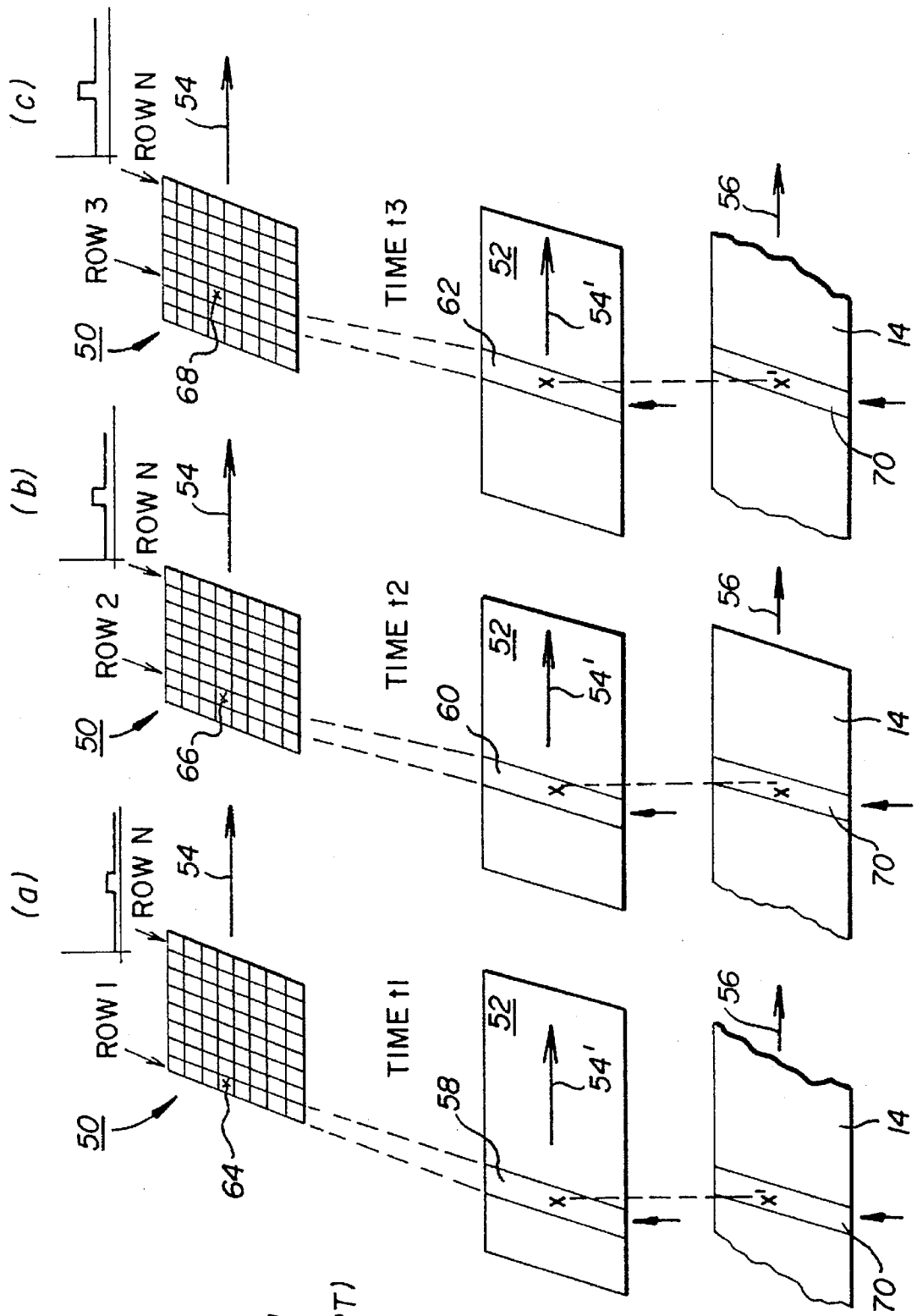
FIG. 1 is a schematic illustration of the operation of a synchronous TDI camera in accordance with the prior art.

As noted initially herein, the present invention is directed to an automated imaging system and method, principally for use to recognize imperfections in a sample of web material, such as photographic film or a paper web. An imaging system based on detection of reflective light off a moving web material is effective for certain surface coating imperfections. However, in products having multiple coating layers, with the possibility of covered layer imperfections, detection of anomalies using transmissive lighting provides for more efficient image analysis. Therefore, the following discussion centers on a coating density analyzer, and an accompanying method, dedicated to a transmissive web lighting approach. In particular, the invention is described in detail herein in connection with the analysis of a predetermined imperfection-type, such as continuous-type imperfections in a moving, sensitized film support. However, those skilled in the art will recognize that the invention is not limited to the specific type of web described. Further, various uses/enhancements are readily conceivable by one skilled in the art, all of which are intended to be encompassed by the appended claims.

Solid state CCD cameras have been described in the above-referenced U.S. Pat. No. 5,533,139 as usable in the detection and analysis of a number of coating imperfections. A two dimensional, 512×512 pixel array, CCD camera is described therein for detecting light transmitted through the moving web that is modulated in intensity by the coating layers. Infrared light transmitted through the web is generated by a light integrating sphere that illuminates the array area in a rectangular video image frame format. Both continuous and strobed illumination may be employed, depending on the mode of detection of streaks or specks. Video image frees of the moving web are derived.

In the U.S. Pat. No. 5,533,139, the preferred commercially available camera was indicated as a Pulnix TM-845 CCD Camera, marketed by Pulnix America, Inc. of Sunnyvale, Calif. This particular camera includes a frame integrating capability, provides a good signal-to-noise ratio and utilizes a cooled element to minimize thermally induced noise. The presence of an integration function in the selected imaging camera is stated therein to be important to the imaging (and automated recognition) of continuous-type imperfections in the moving coated web material. An integration function naturally averages random temporal and spatial variations for enhanced single-to-noise performance. In addition, with integration comes the capability for system operation at extremely low illumination levels, thereby preserving any sensitometric characteristics of the coated web, e.g., if the web comprises coated photographic material.

The integration function described in U.S. Pat. No. 5,533,139 is achieved by a time exposure of the allowable CCD element charge time within each vertical sync time interval. Consequently, the amount of integration provided in the camera of the light transmitted through a given web pixel and impinging on the CCD element is somewhat limited. The smearing of the imaged web pixel is also limited.

In use of the TDI camera in accordance with the invention, the integration time can be increased by the number of rows of CCD elements that successively image the light transmitted through the same web pixel-related area traversing the pixel-related image area. However, not all of the rows of CCD elements image the same web pixel-related area because the web is advanced incrementally through the N pixel-related image areas over the tN clock time cycles so that the N charges do not represent the light transmitted N times through the same pixel-related web area. In this sense, the web pixel-related area is allowed to "creep" through the successive N pixel-related image areas. A "smearing" effect results that is dependent on the number of rows and the disparity between web moving speed and direction and the line shift clock speed of the TDI camera for shifting the charge to the corresponding CCD element in the next row.

Figure 2:
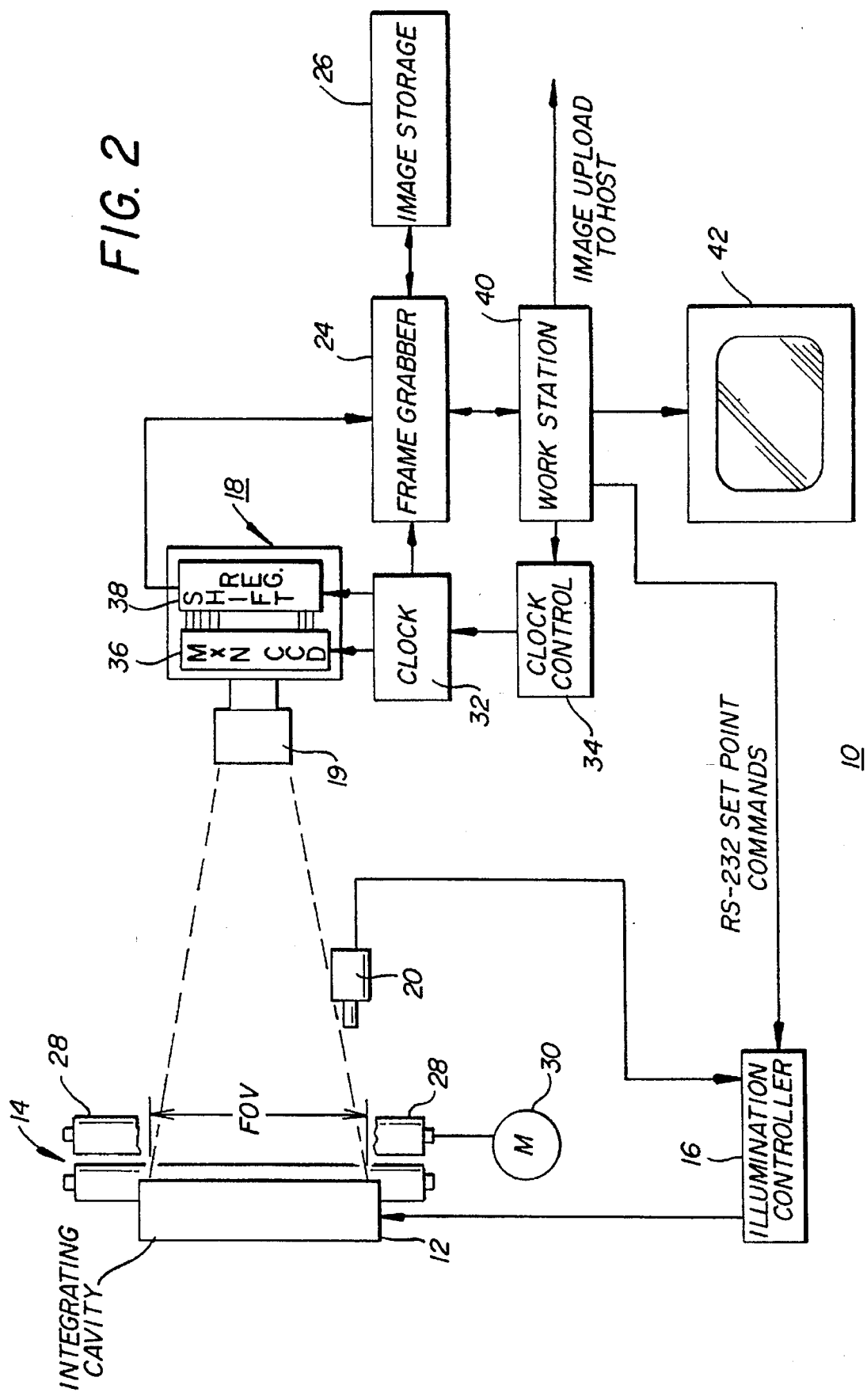
FIG. 2 is a schematic block diagram of the major components of a film scanner employing a TDI camera with a linear light source and operating in the asynchronous mode in accordance with one embodiment of the invention.

FIG. 2 depicts one embodiment of the film scanner, generally denoted 10, constructed pursuant to the present invention. Scanner 10 includes a linear light source 12 described in greater detail in the above-referenced U.S. Pat. No. 5,548,120 which supplies transmissive, infra-red, illumination to a moving, sensitized film web 14 to be scanned and analyzed for imperfections.

Light source 12 is operated under the control of illumination controller 16 as a temporally constant uniform source. A linear light beam of infrared radiation is emitted across the coated web 14 transverse to its direction of motion or length and illuminates a stripe-shaped imaging region of the web 14 of a certain width in the direction of movement of the web 14 corresponding to the number N of rows. For example, the stripe-shaped imaging region or Field of View (FOV) across the web 14 that is illuminated may be about 6 inches (15.2 cm). The illuminated stripe-shaped imaging region is about 0.5 inches (1.2 cm) wide in the direction of movement of the web 14.

The coated web 14 is transported within close proximity (for example, 1–2 cm) to the exit slit of the light source 12. The movement of the web 14 is effected either into or out of the drawing in the length direction of web and orthogonal to the FOV by web drive rollers 28 under the control of web drive 30 in a manner well known in the art. In, this fashion, the web 14 is moved at a certain predetermined rate in a web direction of movement (into or out of the paper in FIG. 2) to present a continuously changing section of the web 14 in the imaging region illuminated with light from the linear light source 12.

An asynchronous TDI CCD camera 18 and feedback photodetector 20 are mounted in proximity of the web 14 in relation to the illuminated stripe-shaped imaging region in the FOV. The TDI camera lens 19 images the moving web region passing through the imaging region onto the internal CCD element array 36 of light sensitive, charge-coupled, image sensor elements extending across the imaging region. Each CCD element in the array 36 is thereby focused on a discrete pixel-related image area of the two-dimensional imaging region in the manner described above with respect to FIG. 1. Each CCD element thereby integrates light from the discrete pixel-related image area and develops a corresponding pixel charge value over an integration time during the shift time cycle as the web 14 is advanced a certain, incremental, distance through the pixel-related image area.

The CCD element array 36 comprises a plurality of N rows by M columns of pixel image sensor CCD elements as shown in FIG. 1. The TDI CCD camera includes a line shift clock 32 (internal or external) for shifting the pixel charge values of the elements of each column from one row to the next row in the manner described above with respect to FIG. 1 and the arrow 54. The line shift clock 32 may be internal to the TDI camera or an external clock control 34 may be provided to operate the clock 32 under the control of the work station 40.

In accordance with the present invention, the shifting of charge values effected by the shift clock signal is asynchronous with respect to the rate of movement of the web 14 through the imaging region. The shift clock signal effects a spatial shift rate of movement that differs from the web rate of movement so that the imaged pixel-related areas in each row of the image region of the web imaged on the successive rows of CCD elements during each clock cycle do not remain constant. A shifting or slippage in the imaged pixel-related areas occurs that is dependent on the degree to which the rate and direction of web movement differs from the spatial image pixel-related area shifting effected by the clock 32.

The movement of the web 14 is preferably opposite to the direction of the shifting of the charge levels through the N rows of CCD elements in response to the line shift clock (arrow 54 of FIG. 1). The preferred opposite direction of web movement (opposite to arrow 56 of FIG. 1) increases the amount of image pixel-related area shift or slippage disparity that can be practically obtained.

In this fashion, unlike the synchronous operation described with respect to FIG. 1, the discrete pixel-related areas of the web 14 imaged by the light sensitive CCD elements in each row change as the pixel charge values are shifted and summed in the successive row light sensitive CCD elements.

An output accumulator or shift register 38 is also provided within the asynchronous TDI camera 18 coupled to the CCD array 36 having M storage locations in a register for receiving the summed charge levels from the Nth row of M CCD elements at the occurrence of each shift clock signal. The output of the shift register 38 representing a video horizontal image line is applied to the frame grabber 24.

The asynchronous TDI CCD camera 18 may take a variety of forms for the line scan of an image of the illuminated stripe of the web. A two-dimensional CCD camera having a 10-bit digital output is sufficient for use as CCD camera 18. Such a TDI camera is available from Dalsa, Inc., Waterloo, CANADA. To provide a good signal-to-noise ratio consistent with the 10-bit (1024 Gray level) dynamic range, the camera may utilize a cooled element or may be operated in a chilled environment to minimize thermally induced dark current noise, as described in the parent U.S. Pat. No. 5,533,139.

Of particular interest in this environment are the expanded Gray scale ranges possible with state-of-the-art 10-bit TDI CCD camera technology. A 10-bit system provides a theoretical response range of 1024 gray levels, and after taking sensor and processing noise into consideration, provides a practical usable range on the order of 9 bits, for the above camera and the ambient temperature conditions. The LSB is affected by thermally related noise in the digitizer absent additional cooling.

The pixel image data from the shift register 38 of the asynchronous TDI CCD camera 18 are applied as 10-bit digital camera output signals each representing the gray level of each pixel of each imaged line of the moving web 14 to a SUN work station 40 through the operation of a Datacube frame grabber 24. Frame grabber 24 includes a digitizer for digitizing the discrete analog charge packets, corresponding to each pixel, a frame array storage matrix, an 8-bit to 10-bit converter and a display. Regardless of the asynchronous TDI CCD camera type used, the frame grabber 24 synchronization can be slaved to the camera clock 32, or vice versa, so that the pixel-to-pixel data corresponds to the frame array storage matrix.

A hard disk image storage 26 is coupled to the frame grabber 24 to enable two-dimensional image archiving of the image frames in order to retrieve the frame data for off-line signal processing and analysis at a later time if needed.

In this manner, the asynchronous TDI CCD camera 18 output signal is formatted by means of the frame grabber 24, which sequentially accumulates digitized representations of two-dimensional image frames which include some degree of smearing of the imaging region of the web 14. Subsequent image data analysis is achieved with software in the work station 40. The digitized image frame signals are applied to the work station 40 which controls operations and retrieves the image data for processing, and an image of the web 14 can be displayed on the monitor 42. The signals may also be uploaded to a host computer and associated external memory, and a printer. The processing of the image frame signals to automatically detect imperfections is further described in the parent U.S. Pat. No. 5,533,139. In addition, the digitized image frame signals may be used to make a print of the detected streaks or sent to an off-line statistical computer and used in other fashions as described in the parent '318 application.

The photodetector 20 samples cavity light output after it has radiated through the coated web 14, and provides a feedback signal for the illumination controller 16 for effectively maintaining constant illumination levels for a range of sensitized coating densities. The illumination controller 16 controls the illumination intensities of the array of LEDs in the linear light source 12 in response to a set point command signal provided by the work station 40 and a feedback signal from the photodetector 20 to maintain a constant average illumination level at the CCD camera 18 for a range of coating densities. Transmitted density values for a wide range of unprocessed B&W and color film codes can be expected to vary for the most part from near 0 through 2.0 optical density units within the wavelengths of interest. The work station 40 provides the set point command signal in RS-232 code to power LED drive circuits in the illumination controller 16 at a pre-defined intensity in the web scanning plane.

In this regard, it is desirable to maintain the illumination intensity of the light stripe falling on the sensitized web 14 low enough to avoid noticeable fogging of the sensitized coatings at the speed of movement of the web. On the other hand, it is also desirable to maintain relatively high exposure levels at the asynchronous TDI CCD camera 18 to optimize signal-to-noise performance. The set point command signal is therefore related to the type of camera employed as well as the web sensitivity. It is desirable to keep the intensity level of the stripe of illumination transmitted through the normal coated web 14 (i.e. webs without imperfections) within a narrow range to maintain the camera at the defined fraction of the saturation level regardless of the coating or base optical density which may vary with film or media type. The feedback signal is therefore employed by the illumination controller to maintain the illumination intensity at the camera plane typically at 80% of the saturation level. The details as to the construction and operation of the linear light source and the illumination controller 16 are set forth in greater detail in the above-referenced '052 application.

Figure 3:
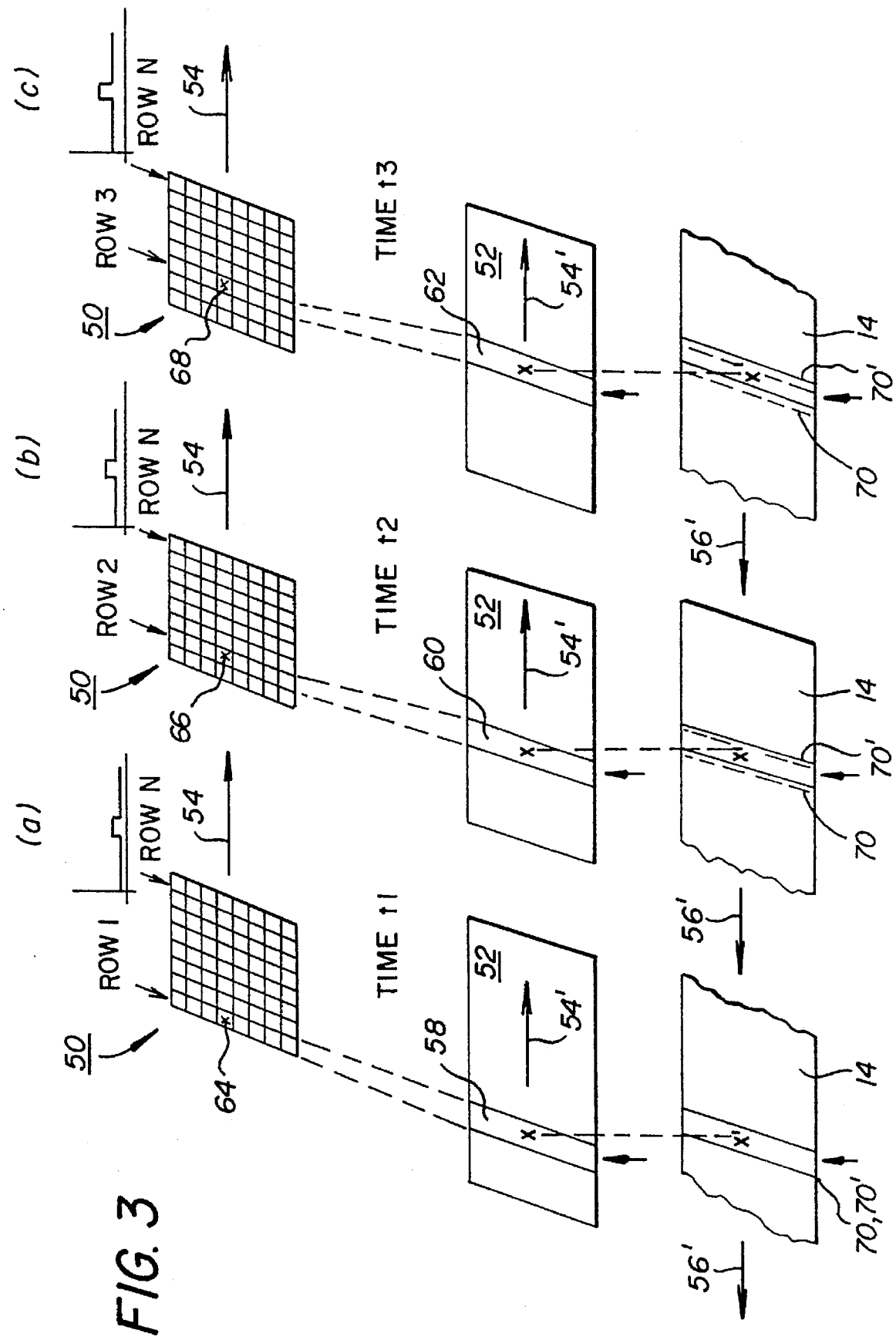
FIG. 3 is a schematic illustration of the creep of the pixel-related image area of the web being moved against the direction of integrated row transfer with respect to the line shift clock of the rows of elements of the CCD array.

Turning to FIG. 3, it illustrates the M×N array pattern 50 of CCD elements of the CCD array 36 of the asynchronous TDI CCD camera 18 in relation to the imaging region 52 of the moving web 14, and the charge accumulation realized as the successive charges in each CCD element in each row 1–N are clocked to the corresponding CCD element in the next row as the web pixel-related image X' is also moved. In this case, the direction of charge transfer for TDI charge accumulation at the clock rate is along the M columns in the opposite direction to the direction of web 14 movement 56'. In addition, the rate of movement in direction 56' is non-synchronous with the clock cycle time.

As shown in FIG. 3, the effective rate of movement is slower than the scan line shift rate effected from scan lines 58–62, so that the pixel-related web stripe area 70 that is initially within the scan line 58 shifts to the left by an incremental amount less than the width of the pixel-related scan lines 58, 60, 62. This shift causes the imaged web stripe area 70' shown at times t2 and t3, et seq., to include a changing increment of the web 14 imaged at each pixel-related web area X' back to the CCD elements 64, 66, 68. The degree of shift is shown exaggerated for emphasis, and it will be understood that the total shift over 96 rows may be less than or somewhat greater than the width of each web stripe area.

Turning to FIG. 4, it illustrates the M×N array pattern 50 of CCD elements of the CCD array 36 of the asynchronous TDI CCD camera 18 in relation to the imaging region 52 of the moving web 14. The charge accumulation realized as the successive charges in each CCD element in each row 1–N are clocked to the corresponding CCD element in the next row as the web pixel-related image area X' is also moved in web movement direction 56" is also shown. In this case, the direction of charge transfer for TDI charge accumulation at the clock rate is along the M columns in the same direction to the web movement direction 56". The effective rate of web movement is faster than the scan line shift rate effected from scan lines 58–62. The pixel-related web stripe area 70 that is initially within the scan line 58 shifts to the right by an incremental amount less than the width of the pixel-related scan lines 58, 60, 62. This shift causes the imaged web stripe area 70' shown at times t2 and t3, et seq., to include a changing increment of the web 14 imaged at each pixel-related web area X' back to the CCD elements 64, 66, 68. Again, the degree of shift is shown exaggerated for emphasis, and it will be understood that the total shift over 96 rows may be less than or somewhat greater than the width of each web stripe area.

FIGS. 3 and 4 therefore depict the smearing effect of the lack of synchronization in the rate of movement of the web 14 in directions 56' and 56" and the effective speed of the shift clock. This causes the pixel-related area X' of the web 14 being imaged by the next CCD element in the same column from times t1-tN to "creep", that is, to shift with the web movement direction 56' or 56".

Random noise contributions of the CCD elements are accumulated along with image charge during the exposure cycle for each pixel site. Because of the cumulative charge transfer over the 96 rows, the noise contributions of individual pixels of the CCD elements in each row are averaged out when the column output signal is clocked into the shift register 38. The total random noise associated with the column output signal is reduced by a factor proportional to the square root of the number N, or about a factor of 9.8 in the preferred embodiment.

Stated another way, the charge levels accumulated in the CCD elements of each row are shifted to the succeeding row or CCD elements and summed with the charge levels therein at a line shift clock frequency that ensures that an asynchronous relationship exists with respect to the rate of movement of the web 14. During the clock cycles over all of the N rows, the pixel areas of the illuminated web shift asynchronously or creep through the corresponding discrete pixel image areas. The accumulated pixel charge values derived from the pixel image areas of the illuminated region of the moving web emphasize imaging of longitudinal streak imperfections in the web due to the asynchronous movement the web.

The system of the present invention thus includes an imaging area within which a predefined continuous-type density imperfection in a moving web is recognized. A light source is provided for substantially uniform illumination of the web while the web is passing through the imaging area. Integration means accumulate density data from the illuminated web and produce integrated image data representative thereof. This data is further accumulated in replicate rows to synthesize an image frame for processing enhancements. An image processor is coupled to the image frame acquisition and integration means and programmed to recognize the predefined continuous-type density imperfection in the web using the produced integrated image data. Such image processing is described in the above-referenced U.S. Pat. No. 5,533,139.

Although several embodiments of the present invention have been illustrated in the accompanying drawings and described in the foregoing detailed description, it will be understood that the invention is not limited to the particular embodiments described herein, but is capable of numerous rearrangements, modifications and substitutions without departing from the scope of the invention. The following claims are intended to encompass all such modifications.

PARTS LIST FOR FIGS. 1-4 coating density analyzer 10
linear light source 12
sensitized film web 14
illumination controller 16
CCD camera 18
focusing lens 19
feedback photodetector 20
frame grabber 24
image storage 26
web drive rollers 28
web drive motor 30
clock 32
clock control 34
CCD element array 36
shift register 38
work station 40
monitor 42
array pattern 50
fixed imaging region 52
line scan direction 54, 54'
web movement direction 56, 56', 56"
successive, adjacent scan lines 58, 60, 62
CCD elements 64, 66, 68
pixel-related web stripe area 70
imaged web stripe area 70'

We claim:

1. A method of detecting streak imperfections in elongated moving webs comprising the steps of:

moving the web to be imaged in a longitudinal direction of movement through an imaging region at a predetermined rate of movement;

illuminating said moving web in said imaging region with light from a light source;

providing a time-delay integrating camera having an array of light sensitive, charge-coupled, image sensor elements, each image sensor element providing discrete light sensitive element pixel charge values dependent on the intensity of light impinging thereon from a discrete pixel image area imaged thereon;

imaging said imaging region of said illuminated moving web onto said time-delay integrating camera array;

shifting the pixel charge values from one discrete light sensitive element to the next discrete light sensitive element across said array during a shift clock cycle time at a shift clock frequency asynchronously related to said rate of movement of said web through said imaging region such that the discrete pixel areas of imaging region imaged by successive light sensitive elements across said array change over the time that the pixel charge values are shifted and summed through all of the successive light sensitive elements;

accumulating the shifted and summed pixel charge values; and processing the accumulated pixel charge values to provide an enhanced image of any streak imperfections in said moving web extending in said direction of movement.

2. The method of claim 1 wherein the processing step further comprises:

serializing the accumulated pixel charge values to produce video image horizontal scan lines;

producing a video display of the projected image of the illuminated region of said moving web from the video image horizontal scan lines; and monitoring the video display to detect streak imperfections in said moving web emphasized by said movement of said web at said predetermined rate during each shift clock cycle time causing the accumulated pixel values to reflect a longitudinal displacement of said moving web.

3. The method of claim 1, wherein said illuminating step includes transmissively uniformly illuminating said web while said web passes through said imaging region.

4. A method of detecting streak imperfections in elongated moving webs employing a time-delay integrating camera comprising the steps of:

moving a web to be imaged through an imaging region at a predetermined rate in a longitudinal direction of movement;

illuminating said moving web in said imaging region with light from a light source;

providing a line shift clock signal defining a clock time cycle during which said moving web is moved in said longitudinal direction an incremental distance;

focusing an imaging region of the moving illuminated web onto a time-delay integrating camera having an array of light sensitive, charge-coupled, image sensor elements, comprising a plurality of N rows of M image sensor elements, each image sensor element integrating light from a discrete fixed pixel-related image area of said imaging region, as a pixel area of said web is moving the incremental distance through the pixel-related image area, into a corresponding pixel charge value over a clock time cycle; and providing said line shift clock signal having said clock time cycle asynchronously with respect to said incremental rate of movement of said web, such that the accumulated pixel charge values derived from the focused pixel images of the illuminated region of said moving web emphasizes imaging of longitudinal streak imperfections in said web due to said movement in said longitudinal direction of said web through the N successive incremental distances.

5. The method of claim 4 wherein said providing step further comprises:

in said time-delay integrating camera, shifting, in response to said line shift clock signal during each clock time cycle, the pixel charge values of each of the M image sensor elements in each row into the corresponding one of the M image sensor elements of the adjacent row and into a shift register for accumulating the pixel charge values over N successive clock time cycles.

6. The method of claim 5 further comprising:

displaying the accumulated pixel charge values derived from the focused image of said illuminated region of said moving web depicting with emphasis longitudinal streak imperfections in said web due to said movement in said longitudinal direction of said web through the N successive incremental distances.

7. The method of claim 6 wherein the displaying step further comprises:

serializing the accumulated pixel charge values in said shift register to produce video image horizontal scan lines;

producing a video display of the focused image of the illuminated region of said moving web from the video image horizontal scan lines; and monitoring the video display to detect streak imperfections in said moving web emphasized by said movement of said web at said predetermined rate during each clock time cycle causing the accumulated pixel values to reflect a longitudinal displacement of said moving web.

8. The method of claim 4, wherein said illuminating step includes transmissively uniformly illuminating said web while said web passes through said imaging region.

9. Apparatus for detecting streak imperfections in moving webs comprising:

means for moving said web to be imaged in a longitudinal direction of movement through an imaging region at a predetermined rate;

means for illuminating said moving web in said imaging region with light from a light source;

a time-delay integrating camera having an array of light sensitive, charge-coupled, image sensor elements extending across said imaging region, each image sensor element providing discrete light sensitive element pixel charge values dependent on the intensity of light falling thereon;

means for imaging said imaging region of said moving illuminated web region onto said array of light sensitive, charge-coupled, image sensor elements of said time-delay integrating camera, whereby a discrete pixel area of said imaging region is imaged on each sensor element;

means for shifting the pixel charge values from one discrete light sensitive element to the next light sensitive element across said array with respect to the direction of movement of said web at a fixed line shift frequency asynchronously with respect to said rate of movement of said web through the imaging region, such that the discrete pixel areas imaged by said light sensitive elements change as the pixel charge values are shifted and summed in successive light sensitive elements;

means for accumulating the shifted and summed pixel charge values; and means for processing the accumulated pixel charge values to provide an enhanced image of imperfections in said moving web extending lengthwise in said direction of movement.

10. The apparatus of claim 9 wherein the processing means further comprises:

means for serializing said accumulated pixel charge values in said shift register to produce video image horizontal scan lines;

means for producing a video display of the focused image of the illuminated region of said moving web from the video image horizontal scan lines; and means for monitoring the video display to detect streak imperfections in said moving web emphasized by said movement of said web at said predetermined rate during each clock time cycle causing the accumulated pixel values to reflect a longitudinal displacement of said moving web.

11. The apparatus of claim 9, wherein said illuminating means includes means for transmissively uniformly illuminating said web while said web passes through said imaging region.

12. Apparatus for detecting streak imperfections in moving webs comprising:

means for moving a web to be imaged through an imaging region at a predetermined rate in a longitudinal direction of movement;

means for illuminating said moving web in the imaging region with light from a light source;

means for providing a line shift clock signal defining a clock time cycle during which said moving web is moved in said longitudinal direction an incremental distance;

a time-delay integrating camera having an array of light sensitive, charge-coupled, image sensor elements, comprising a plurality of N rows of M image sensor elements, each image sensor element integrating light from a discrete fixed pixel-related image area of the imaging region, as said web is moving said incremental distance through said pixel-related image area, into a corresponding pixel charge value over said clock time cycle;

means for focusing an image of the moving illuminated web onto said array of light sensitive, charge-coupled, image sensor elements of said time-delay integrating camera;

means for providing said line shift clock signal having said clock time cycle asynchronously with respect to said incremental rate of movement of said web, such that the accumulated pixel charge values derived from the focused pixel images of the illuminated region of said moving web emphasizes imaging of longitudinal streak imperfections in said web due to said movement in said longitudinal direction of said web through the N successive incremental distances.

13. The apparatus of claim 12 further comprising:

in said time-delay integrating camera, a shift register and means for shifting, in response to said line shift clock signal during each clock time cycle, the pixel charge values of each of said M image sensor elements in each row into said image sensor elements of the adjacent row and into said shift register for accumulating the pixel charge values over N successive clock time cycles.

14. The apparatus of claim 13 further comprising:

means for displaying the accumulated pixel charge values derived from the focused image of the illuminated region of said moving web depicting with emphasis on longitudinal streak imperfections in said web due to said movement in said longitudinal direction of said web through the N successive incremental distances.

15. The apparatus of claim 12, further comprising:

in said time-delay integrating camera, means for shifting, in response to said line shift clock signal during each clock time cycle, the pixel charge values of each of said M image sensor elements in each row into the image sensor elements of the adjacent row; and means for accumulating the shifted and summed pixel charge values into a shift register for accumulating the pixel charge values over M successive clock time cycles; and further comprising:

means for displaying the accumulated pixel charge values derived from the focused image of the illuminated region of said moving web depicting with emphasis longitudinal streak imperfections in said web due to said movement in said longitudinal direction of said web through the N successive incremental distances.

16. The apparatus of claim 15 wherein the displaying means further comprises:

means for serializing the accumulated pixel charge values in said shift register to produce video image horizontal scan lines;

means for producing a video display of the focused image of the illuminated region of said moving web from the video image horizontal scan lines; and means for monitoring the video display to detect streak imperfections in said moving web emphasized by the movement of said web at said predetermined rate during each clock time cycle causing the accumulated pixel values to reflect a longitudinal displacement of said moving web.

17. The apparatus of claim 12, wherein said illuminating means includes means for transmissively uniformly illuminating said web while said web passes through said imaging region.

* * * * *